(12) United States Patent
Parks, II et al.

(10) Patent No.: US 8,248,612 B2
(45) Date of Patent: Aug. 21, 2012

(54) OXYGEN CONCENTRATION SENSORS AND METHODS OF RAPIDLY MEASURING THE CONCENTRATION OF OXYGEN IN FLUIDS

(75) Inventors: James E. Parks, II, Knoxville, TN (US); William P. Partridge, Jr., Oak Ridge, TN (US)

(73) Assignee: UT-Batelle, LLC, Oak Ridge, TN (US)

( * ) Notice: Subject to any disclaimer, the term of this patent is extended or adjusted under 35 U.S.C. 154(b) by 131 days.

(21) Appl. No.: 12/843,121

(22) Filed: Jul. 26, 2010

(65) Prior Publication Data

US 2012/0019829 A1 Jan. 26, 2012

(51) Int. Cl.
*G01N 21/00* (2006.01)
(52) U.S. Cl. ......... 356/437; 356/432; 356/436; 356/438
(58) Field of Classification Search .......... 356/432–444, 356/317–320, 326; 250/339.12, 341.2, 459.1, 250/227.14, 461.1; 422/82.07, 82.06; 128/634, 128/633; 436/136, 138, 172, 178
See application file for complete search history.

(56) References Cited

U.S. PATENT DOCUMENTS

| | | | | |
|---|---|---|---|---|
| 4,476,870 | A | * | 10/1984 | Peterson et al. ............... 600/312 |
| 5,034,189 | A | * | 7/1991 | Cox et al. ......................... 422/52 |
| 5,043,286 | A | * | 8/1991 | Khalil et al. ................... 436/136 |
| 5,315,993 | A | * | 5/1994 | Alcala ............................ 600/341 |
| 5,341,676 | A | * | 8/1994 | Gouterman et al. ............ 73/147 |
| 5,409,666 | A | * | 4/1995 | Nagel et al. ................ 422/82.07 |
| 5,742,064 | A | | 4/1998 | Infante |
| 5,885,843 | A | * | 3/1999 | Ayers et al. ................... 436/136 |
| 7,410,793 | B2 | | 8/2008 | Boege et al. |
| 7,414,726 | B1 | * | 8/2008 | Bambeck ...................... 356/436 |
| 2002/0173922 | A1 | * | 11/2002 | Potyrailo ........................ 702/39 |
| 2003/0190262 | A1 | * | 10/2003 | Blazewicz et al. .............. 422/94 |
| 2004/0084623 | A1 | * | 5/2004 | Long et al. ................ 250/339.12 |
| 2009/0310127 | A1 | | 12/2009 | Parks, II et al. |

* cited by examiner

*Primary Examiner* — Sang Nguyen
(74) *Attorney, Agent, or Firm* — Colin L. Cini

(57) ABSTRACT

Provided are sensors and methods of measuring the oxygen concentration of a fluid. An excitation light source is in optical communication with a transducer for transmitting an excitation light that is at least partially absorbed by the transducer. The transducer has a property of photoluminescence, and enters a higher energy state by at least partially absorbing the excitation light and enters a lower energy state through radiation of emitted light, thus producing spectral indicia. A light detection system, which is also in optical communication with the transducer, processes the spectral indicia to determine the concentration of oxygen in the fluid.

15 Claims, 4 Drawing Sheets

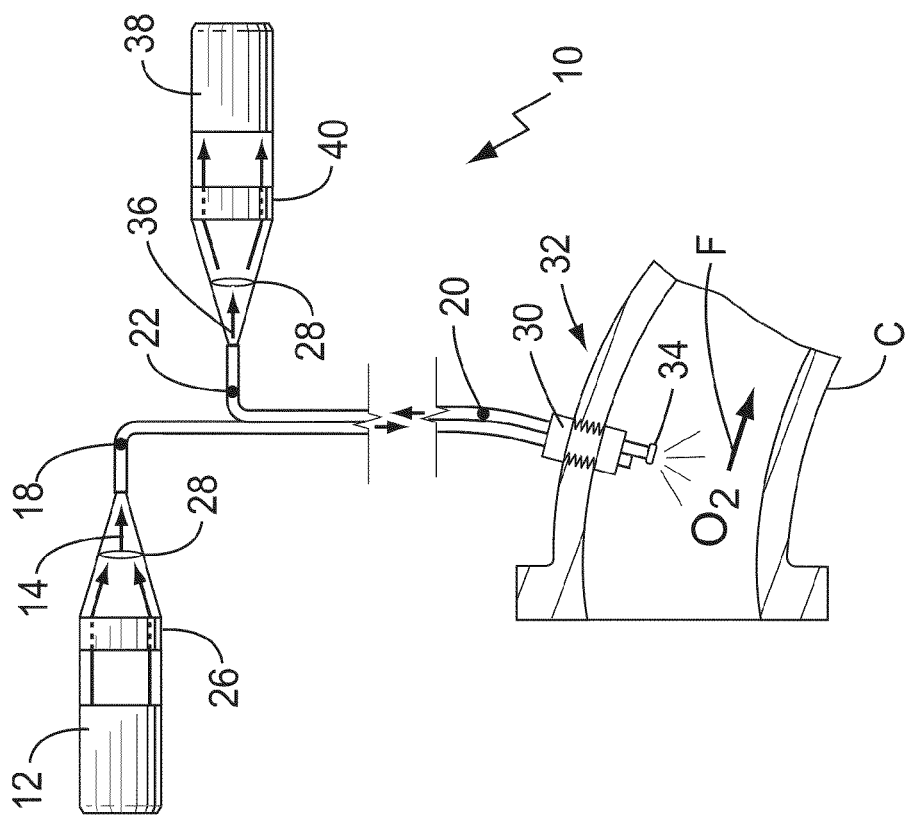
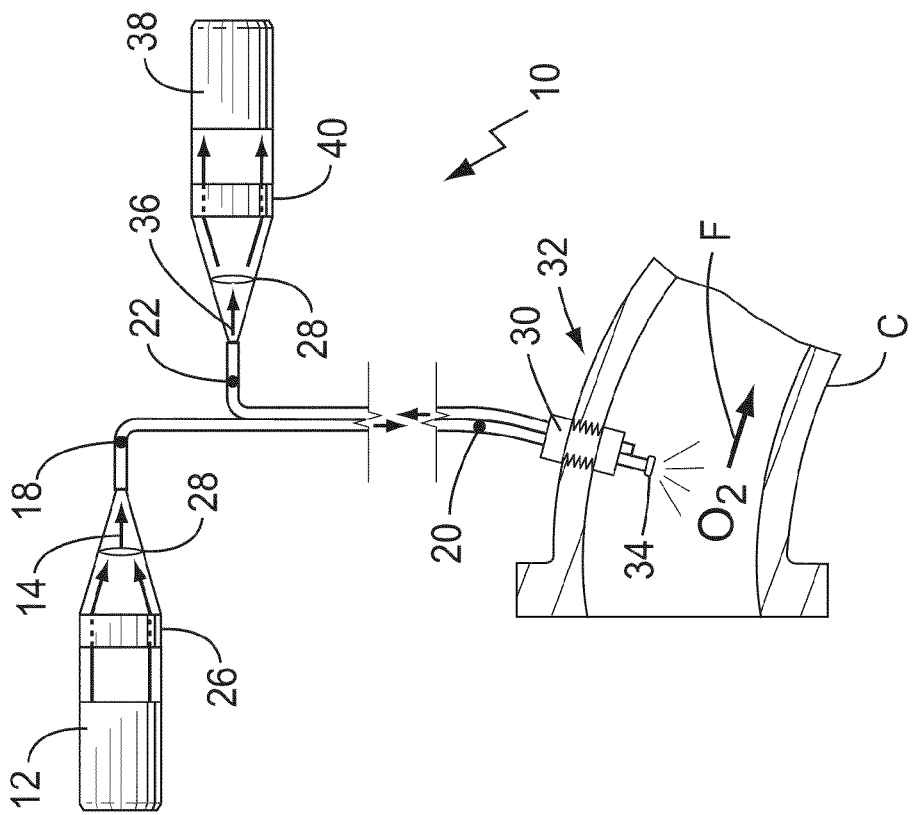

OXYGEN CONCENTRATION SENSORS AND METHODS OF RAPIDLY MEASURING THE CONCENTRATION OF OXYGEN IN FLUIDS

STATEMENT REGARDING FEDERALLY SPONSORED RESEARCH AND DEVELOPMENT

This invention was made with government support under Contract No. DE-AC05-00OR22725 awarded by the U.S. Department of Energy. The government has certain rights in the invention.

THE NAMES OF THE PARTIES TO A JOINT RESEARCH AGREEMENT

None.

BACKGROUND OF THE INVENTION

1. Field of the Invention

The present disclosure relates to sensors and methods for use in rapid measurement of the concentration of oxygen in fluids.

2. Description of the Related Art

The measurement of oxygen concentrations of fluids is important in many technical, scientific, energy, medical and recreational fields. For example, oxygen sensors are used in medical applications such as anesthesia monitors, respirators and oxygen concentrators. Scuba divers use oxygen sensors to monitor the concentration of breathing gas mixes in open and closed circuit breathing devices. In marine biology, oxygen measurements are done to measure respiration of a community or an organism. Another common application is the measurement of the oxygen concentration in an exhaust gas stream of an internal combustion engine. The Environmental Protection Agency considers carbon monoxide (CO), oxides of nitrogen ($NO_x$), hydrocarbons (HCs), and Particulate Matter (PM) as pollutants of primary concern from vehicles with other species also potentially harmful (lead, sulfur dioxide, benzene, etc.). Oxygen concentration measurements are used by onboard systems to minimize these emissions.

Traditional oxygen sensors installed in internal combustion engines measure the proportion of oxygen remaining in the exhaust gas, and by knowing the volume and temperature of the air entering the cylinders among other parameters, an electronic control unit (ECU) determines the amount of fuel required to achieve the correct stoichiometric ratio (14.7:1 air:fuel by mass for gasoline for example). These sensors are typically made of a ceramic cylinder plated inside and out with porous platinum electrodes. The sensors operate by measuring the difference in oxygen between the exhaust gas and the external air, and generate a voltage or change their resistance depending on the difference between the two. Because the sensors only work effectively when heated, an integrated heater brings the temperature up quickly to reduce the zero-response time associated with engine start up.

These oxygen sensors are normally threaded into a port in the exhaust system, downstream of the exhaust manifold and upstream of the catalytic converter. Some vehicles have sensors upstream and downstream of the catalytic converter; e.g., to meet U.S. regulations requiring that all emissions components be monitored for failure. Implementation of these oxygen sensors at other locations in the engine system can be limited by their sensitivity to pressure. Such sensitivity makes oxygen measurement in intake and exhaust manifolds difficult for boosted engines, e.g., turbocharged or supercharged.

BRIEF SUMMARY OF THE INVENTION

Provided are sensors for use in measuring the concentration of oxygen in a fluid. An example sensor includes a transducer having a photoluminescence property. An excitation light source, in optical communication with the transducer, transmits an excitation light that is at least partially absorbed by the transducer. The transducer enters a higher energy state by at least partially absorbing the excitation light and enters a lower energy state at least partially through radiation of emitted light. The transition from one energy state to another produces spectral indicia having intensity and a lifetime. A light detection system, which is also in optical communication with the transducer, processes the spectral indicia to determine the concentration of oxygen in the fluid.

Also provided are methods for use in measuring the concentration of oxygen in a fluid. An example method includes a first step of providing a transducer having a photoluminescence property. Next, the transducer is energized through at least partial absorption of excitation light transmitted by an excitation light source that is in optical communication with the transducer. Next, the transducer generates spectral indicia as the transducer transitions to a higher energy state from a lower energy state through the at least partial absorption of the excitation light, and as the transducer transitions to a lower energy state from the higher energy state through radiation of emitted light. Finally, a light detection system that is in optical communication with said transducer processes the spectral indicia to determine the oxygen concentration of the fluid.

BRIEF DESCRIPTION OF THE SEVERAL VIEWS OF THE DRAWINGS

A more complete understanding of the disclosed examples will be more readily understood by reference to the following detailed description when considered in conjunction with the accompanying drawings, where like numerals indicate common elements among the various figures.

FIG. 2 is a plan view of another sensor in accordance with another example of the present disclosure.

FIG. 3 is a plan view of a sensor in accordance with another example of the present disclosure.

DETAILED DESCRIPTION OF THE INVENTION

Figure 1:
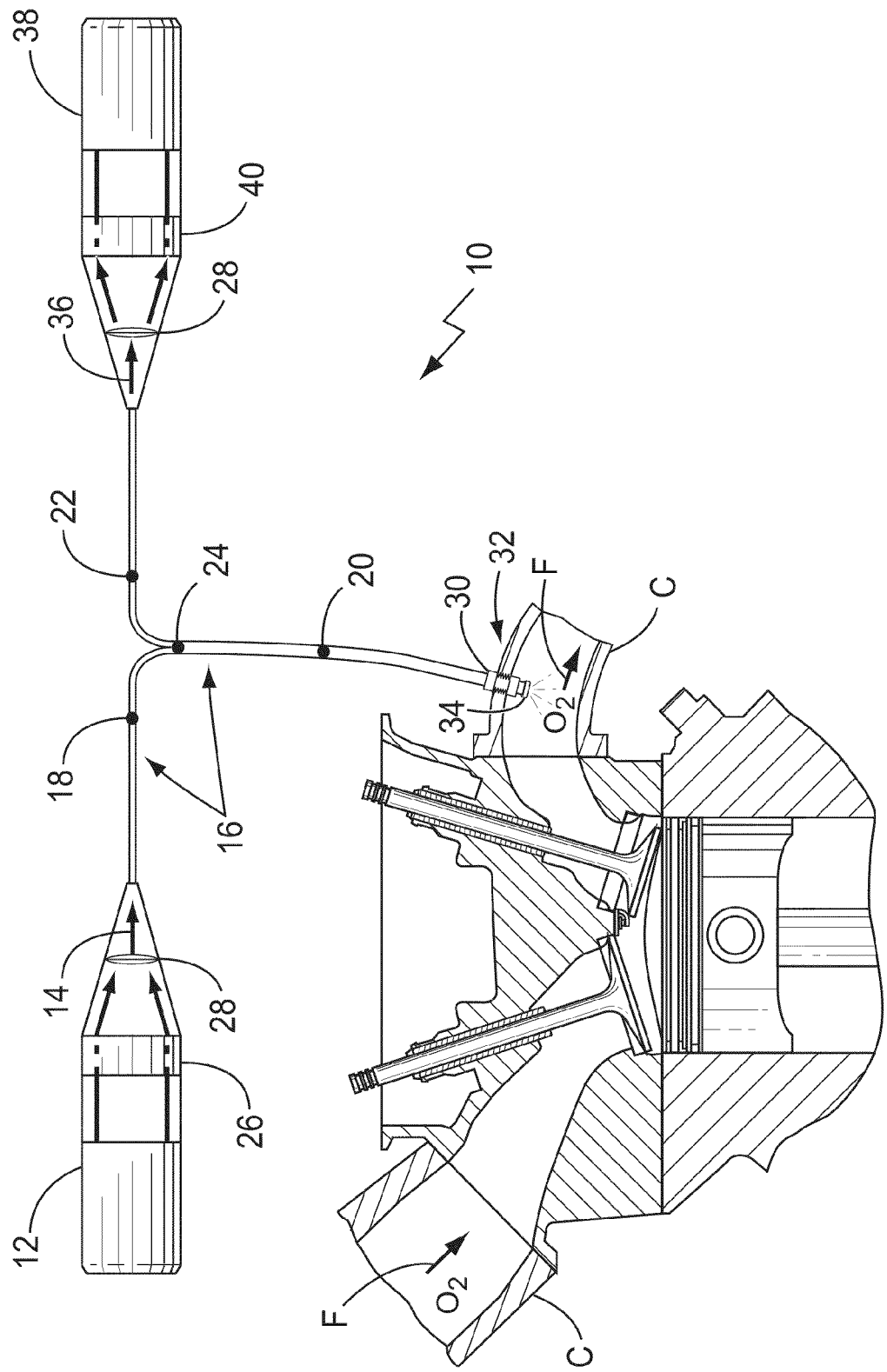
FIG. 1 is a partial sectional view illustrating a sensor, in accordance with an example of the present disclosure, installed in a fluid-carrying component of an internal combustion engine.

With reference first to FIG. 1, an example sensor 10 for rapid measurement of oxygen concentration in a fluid F is illustrated. The fluid F in this example is directed within a fluid-carrying component C, such as an intake manifold or exhaust manifold of an internal combustion engine. An excitation light source 12 projects excitation light 14, via optical communication, at the fluid F being sampled. The fluid F to be sampled can be any liquid or gas, and in this example, the fluid F contains Oxygen ($O_2$). Optical communication includes both the direct projection of excitation light 14 at the fluid F, or transmission of excitation light 14 through one or more optical communication devices interposed between the excitation light source 14 and the fluid F.

In the present example, the excitation light 14 is first directed into a fiber optic assembly 16, including an excitation leg 18, a sensing leg 20, and a detection leg 22. The excitation leg 18 and the detection leg 22 merge together into the sensing leg 20, in a "Y" configuration, at a junction 24. The optical fibers making up each of the legs 18, 20, 22 may be solid fibers made from fused-silica coated in polyimide for example. The optical fibers, typically less than approximately 700 microns in diameter, allow for minimally invasive measurements of oxygen concentration in both high and low temperature fluids F.

The excitation light 14 is generated by any suitable, excitation light source 12 known in the art of fluorescence spectrographic analysis. Various sources 12 such as a light emitting diode (LED), a laser diode, a non-diode laser, an incandescent device and a fluorescent device may be used. In one example, a 450 nm Blue LED was used as the excitation light source 12. In some examples, the excitation light source 12 may first pass through a bandpass filter 26 and/or a collimating lens 28, before entering the excitation leg 18. The bandpass filter 26 removes certain wavelengths of light from the excitation light 14, while the collimating lens 28 couples the excitation light 14 into the optical excitation leg fiber.

Once through the bandpass filter 26 and collimating lens 28, the excitation light 14 enters the excitation leg 18 and is then directed into the sensing leg 20 at the junction 24. The sensing leg 20 may include means 30 for fastening and sealing the sensing leg 20 to a fluid-carrying component C, for example, an intake manifold or an exhaust manifold of an internal combustion engine. A compression fitting, adhesive material, braze material, stoppers or other fastening and sealing means 30 safely and operably affix the sensor 10 to the component C while preventing leakage of the fluid F. In other examples, the sensing leg 20 is simply placed in contact with the fluid F with less robust fastening and sealing means 30, or no fastening and sealing means 30 at all.

Disposed at a terminus 32 of the sensing leg 20 is a transducer 34 that is capable of photoluminescence. The transducer 34 at least partially absorbs the excitation light 14, entering a higher energy state (e.g. phosphoresces) from a lower energy state, and also radiates an emitted light 36 as the transducer 34 enters a lower energy state from a higher energy state. While partial absorption of excitation light 14 by the transducer 34 is sufficient to allow the sensor 10 to function, it is preferable to have high absorption or full absorption for optimized functionality. The transition between energy states creates spectral indicia, with emissive intensity and a lifetime being indicative of the oxygen concentration of the fluid F of interest. In general, decreased emissive intensity and decreased spectral lifetime of the emitted light 36 is indicative of a higher oxygen concentration in the fluid F being sampled. The ability to rapidly measure oxygen concentrations in fluids is especially beneficial for optimizing the power and emissions output of internal combustion engines. The complete fluorescence process (e.g. absorption to emission) occurs very rapidly, approximately 200 nanoseconds, and is relatively short when compared with the period of a single engine combustion cycle, which occurs in approximately 50 milliseconds at 2400 revolutions per minute.

The emitted light 36 enters a light detection system 38 for processing of the spectral indicia through optical communication. Optical communication includes the direct projection of emitted light 36 to the light detection system 38, or transmission of emitted light 36 through one or more optical communication devices interposed between the emitted light 36 and the light detection system 38. In the present example, the emitted light 36 is directed into the sensing leg 20 of the fiber optic assembly 16, and then through the junction 24 to the detection leg 22 before entering the light detection system 38. In some examples, the emitted light 36 may first be directed through a collimating lens 28 and/or a filter 40 e.g., band-pass filter or long-pass filter, before entering the light detection system 38. The collimating lens 28 directs the beam towards the filter 40, which attenuates shorter excitation wavelengths and transmits longer wavelengths of the emitted light 36 prior to entering the light detection system 38.

Processing of the spectral indicia (e.g. radiant energy and lifetime) from the emitted light 36 can be carried out using any suitable light detection system 38 that is sensitive to the wavelength(s) of light of interest. For example, a light detection system 38 may include a spectrometer that disperses light based on wavelength or by other means. As an example, a fluorescent light detection system 38 may include a series of band-pass filters to select specific wavelength regions of the emitted light 36. In one example, a 532-nm band-pass filter was used. As another example, a fluorescent light detection system may include a system where the ultimate detection of light is performed by any number of a variety of detectors including, but not limited to, photomultiplier tubes, diode detectors, charge coupled device (CCD) arrays, diode arrays, and the like.

With reference now to FIG. 2, another example of a sensor 10 affixed to a fluid-carrying component C is illustrated. Unlike the sensor 10 in the previous example, the excitation leg 18 is separate from, and does not merge with, the detection leg 22 at a junction in a "Y" configuration. Instead, the sensing leg 20 is merely an extension of the excitation leg 18. Excitation light 14 is directed into the excitation leg 18 to the transducer 34 disposed on the sensing leg 20. In some examples, the transducer 34 is disposed at the terminus 32 of the sensing leg 20 (shown), and in other examples the transducer 34 is disposed at a position along the sensing leg 20. The transducer 34 at least partially absorbs the excitation light 14, thus entering a higher energy state from a lower energy state. The transducer 34 radiates an emitted light 36 as it enters a lower energy state from a higher energy state. The emitted light 36 is then directed into and along the detection leg 22. The excitation light source 12 and the light detection system 38 are as described in the first example.

With reference now to FIG. 3, yet another example of a sensor 10 is illustrated. In this example, the excitation leg 18 is also separate from, and does not merge with, the detection leg 22 as in the first sensor 10 example. The sensing leg 20 is simply an extension of the detection leg 22. Excitation light 14 is directed into and along the excitation leg 18 and exits through a terminus 32 towards the transducer 34 disposed on the sensing leg 20. In some examples, the transducer 34 is disposed at the terminus 32 of the sensing leg 20 (shown), and in other examples the transducer 34 is disposed at a position along the sensing leg 20. The transducer 34 at least partially absorbs the excitation light 14, entering a higher energy state from a lower energy state. The transducer 34 radiates an emitted light 36 as the transducer 34 enters a lower energy state from a higher energy state. The emitted light 36 is then directed into and along the sensing leg 20 to the detection leg 22. The excitation light source 12 and the light detection system 38 are as described in the first example.

Figure 4:
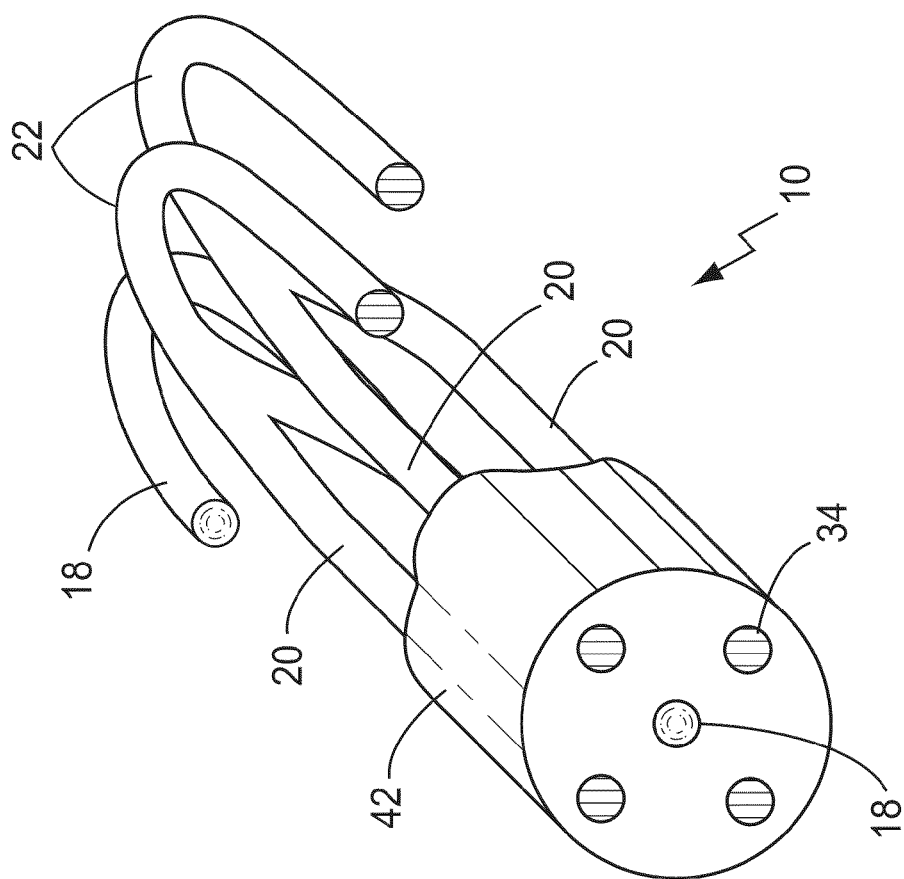
FIG. 4 is a partial perspective view of a sensor in accordance with another example of the present disclosure.

With reference now to FIG. 4, yet another example of a sensor 10 is illustrated. In this example, the excitation leg 18 is also separate from, and does not merge with, the detection leg 22 as in the first sensor 10 example. Here, a single excitation leg 18 is proximate a plurality of transducers 34 disposed at the termini of a plurality of sensing legs 20. The individual sensing legs 20 may merge together into one or more detecting legs 22, before entering one or more light detection systems 38 (not shown). A probe 42 with a body made of epoxy or rubber, for example, secures the legs 18 and 20 in a spaced arrangement. The light cones from the excitation leg 18 and the detecting legs 22 must overlap at the transducer 34. In some examples, there is a window between the ends and the transducer material (not shown).

Figure 5:
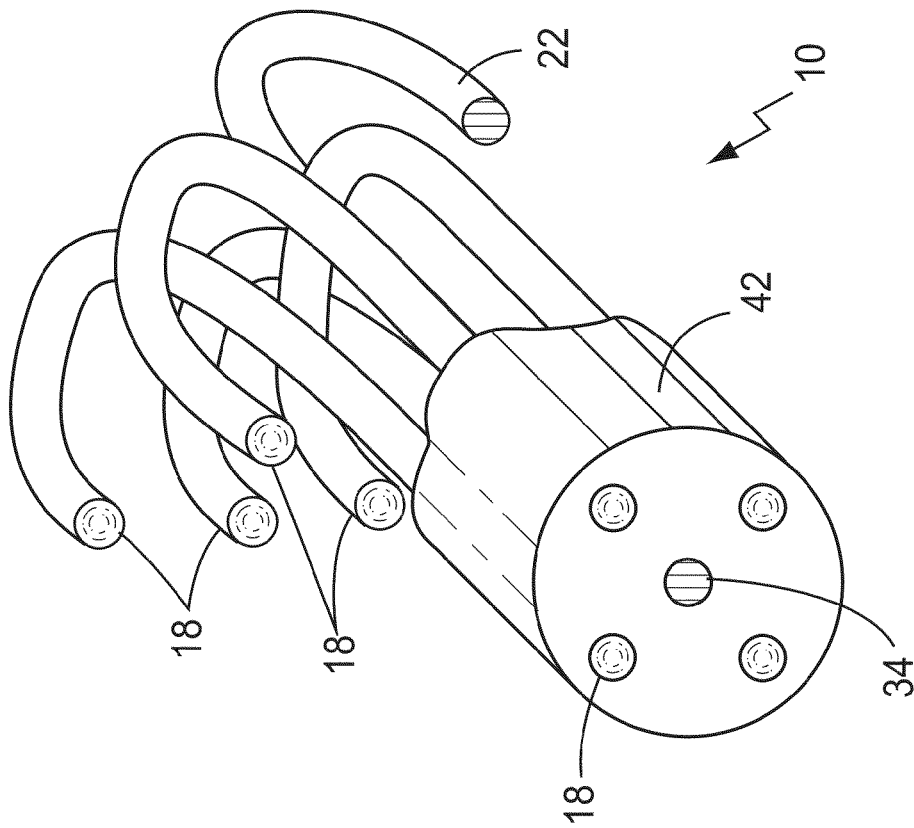
FIG. 5 is a partial perspective view of a sensor in accordance with another example of the present disclosure.

With reference now to FIG. 5, yet another example of a sensor 10 is illustrated. In this example, the excitation leg 18 is also separate from, and does not merge with, the detection leg 22 as in the first sensor 10 example. Here, a plurality of excitation legs 18 are proximate a single transducer 34 disposed at the terminus of a sensing leg 20 (not shown). The plurality of excitation legs 18 may extend from one or more excitation legs 22 and the sensing leg 20 merges into a detection leg 22, before entering one or more light detection systems 38 (not shown). A probe 42 with a body made of epoxy or rubber, for example, secures the legs 18 and 20. Please note that FIGS. 4 & 5 illustrate a sampling of the many possible examples of detection legs 22, excitation legs 18, sensing legs 20 and transducers 34 that are contemplated.

The transducer 34 in each of the previous examples has the property of photoluminescence, and is comprised of a phosphorescence-type or a florescence-type material coated on a portion of the sensing leg 20 of the fiber optic assembly 16. In high-temperature applications (e.g. above 200 Degrees Celsius), rare-earth, metal doped phosphors such as $MgFGeO_6$:Mn and $Y_2O_3$:Eu, for example, may be used. In low-temperature applications (e.g. 0 Degrees Celsius), organometallic Pt and Ru complexes, for example, may be used.

The transducer 34 coating material may be glued to the optical fibers using a refractory binder or sputtering techniques may be used to apply the coating for example. In another example, the coating is applied to the fiber optic cable terminus using a sol-gel process, where a sol is a solution with particles suspended in it. Using hydrolysis and polycondensation, metal oxide particles in the sol form long polymers (chains) that span the entire sol, thus forming the gel. The gel eventually becomes a solid as solvents, such as Tetraethylorthosilicate (TEOS), and water ($H_2O$) evaporate out of the gel.

Physical characteristics of the transducer 34 such as porosity, surface area and density are controlled by the selection of precursors, pH, catalyst, $H_2O$ to TEOS ratio, and solvent amount. A $H_2O$ to TEOS ratio of approximately 4.0 to 1.0 is, in theory, the lowest ratio needed for complete hydrolysis. Intermediate ratios balance surface area, porosity and bulk density parameters. Excess $H_2O$ forms a gel with large, unevenly distributed pores and slower transducer response time. Excess TEOS leaves partially hydrolyzed alkoxides and phase separation. Raising the pH away from isoelectric point prior to dipping to increase condensation rate decreases the tendency for the material to crack during thermal aging, but also increases the amount of light-scattering silica particles.

Optimizing the physical properties of the materials was achieved by experimenting with the addition of excess solvent and processing the sol-gel with a two-step, acid/base-catalyzed approach. For the excess solvent experiment, EtOH, $H_2O$, $NHO_3$, and TEOS (molar ratios 24:4:0.0002:1) were mixed and sealed for two weeks. 1.0 mL aliquots were taken and 0.01 M NaOH was added to achieve a neutral pH. For the two-step acid-catalyzed hydrolysis and base-catalyzed condensation experiment, EtOH, $H_2O$, $NHO_3$, and TEOS (molar ratios 3:4:0.005:1) were mixed and sealed for two weeks. 1.0 mL aliquots were taken and 0.01 M NaOH was added to achieve a neutral pH.

Once the gel material was created using one of the aforementioned methods, the terminus of an optical fiber was dip coated. Dip coating provides for a controlled deposit of an indicator doped layer e.g., phosphor layer onto the terminus of the optical fiber. The optical fibers were first soaked in acid to etch them prior to dipping into the doping material at a rate of approximately 5 cm/min. One or more dips were necessary to achieve a suitable material structure and surface condition of the coating. For example, one to three dips were found to be suitable in most cases.

After dip coating, the coated terminus was thermally aged to enhance the structural network and attachment of the coated material to the optical fiber. For example, a stepped heating cycle from room temperature to 200 Degrees Celsius at 3 Degrees Celsius per minute and from 200 Degrees Celsius to 450 Degrees Celsius at 10 Degrees Celsius per minute provided an adequate material structure.

The sensitivity of the transducers was not lost over time. The sensor is capable of measurement over a broad temperature range of approximately 0 Degrees Celsius to 200 Degrees Celsius. The very small sensing leg 20, typically less than approximately 700 microns in diameter, is minimally invasive and improves the spatial and temporal resolution of oxygen concentration measurements in fluids. Multiple transducers 34 may be used and positioned throughout a fluid or a single transducer 34 may be traversed across a fluid to measure spatial variations (i.e., distributions) in the oxygen concentration.

Figure 6:
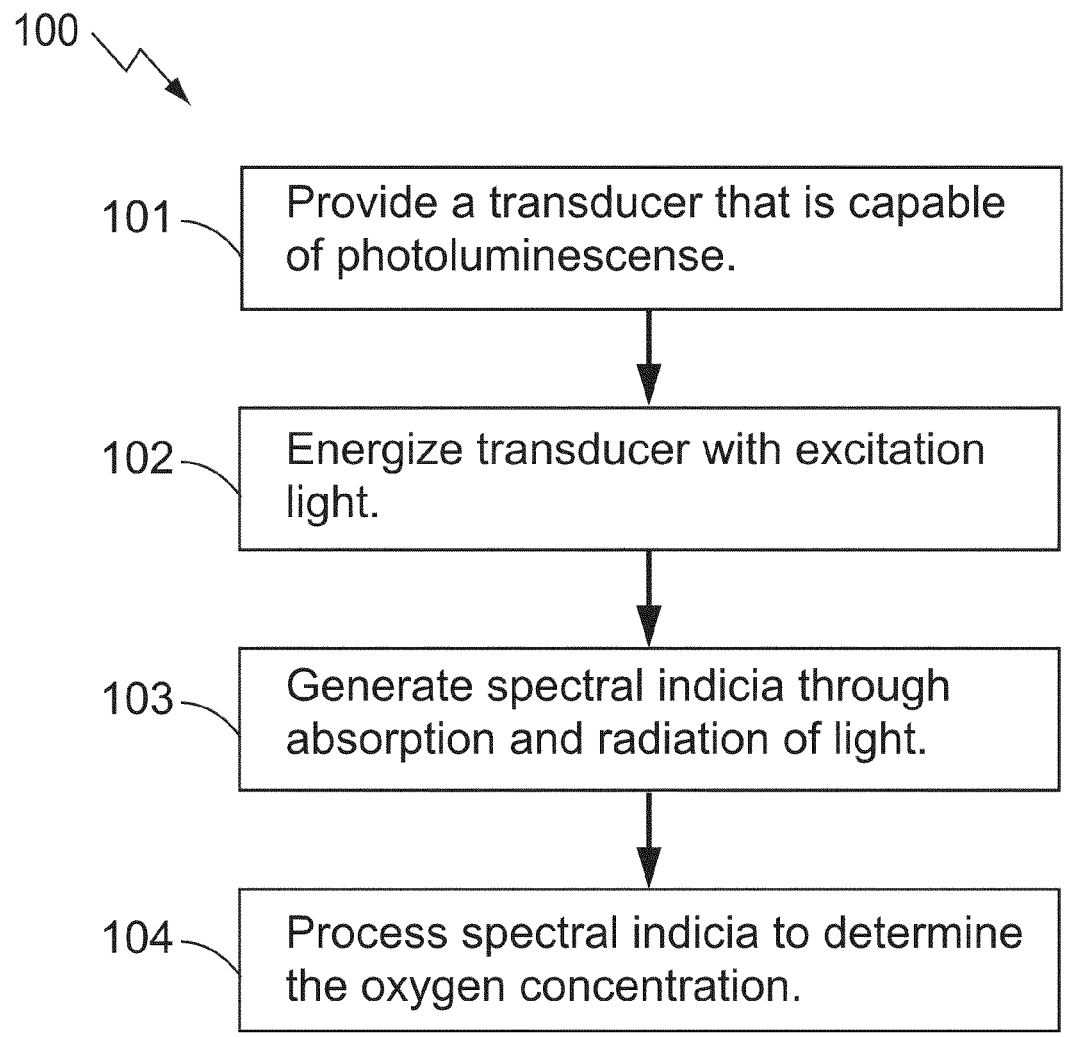
FIG. 6 is a block diagram illustrating the various method steps of rapidly measuring the concentration of oxygen in fluids with one or more example sensors of the present disclosure.

With reference finally to FIG. 6, various method steps 100 for rapidly measuring the oxygen concentration of a fluid F of interest, using one of the example sensors 10 described above, are illustrated. In a first step represented by block 101, a transducer 34 that is capable of photoluminescence is provided to the fluid F of interest. In a second step represented by block 102, the transducer 34 is energized by at least partial absorption of excitation light 18 transmitted by an excitation light source 12 that is in optical communication with the transducer 34. Optical communication includes both the direct projection of excitation light 14 at the fluid F, or transmission of excitation light 14 through one or more optical communication devices such as a fiber optic assembly 16. In the third step represented by block 103, the transducer 34 generates spectral indicia as the transducer 34 transitions to a higher energy state from a lower energy state through the at least partial absorption of the excitation light 14, and as the transducer 34 transitions to a lower energy state from the higher energy state through radiation of emitted light 36. In a final step represented by block 104, the spectral indicia are processed with a light detection system 38 that is in optical communication with said transducer 34 to determine the oxygen concentration of the fluid F.

While the examples presented illustrate specific examples in the field of internal combustion engine systems, it is to be recognized that the apparatuses and methods disclosed may be used in many additional fields including, but not limited to, technical, scientific, energy, medical and recreational fields. Other alternatives, modifications, equivalents, and variations will become apparent to those skilled in the art having reviewed the figures and read the foregoing description. Accordingly, the invention is intended to embrace those alternatives, modifications, equivalents, and variations as fall within the broad scope of the appended claims. The technology disclosed and claimed herein is available for license in specific fields of use by the assignee of record.

What is claimed is:

1. An apparatus for rapidly sensing the oxygen concentration of a fluid comprising:
   a transducer capable of photoluminescence and configured to be installed in an intake manifold of an internal combustion engine;
   an excitation light source in optical communication with said transducer for transmitting an excitation light that is at least partially absorbed by said transducer;
   a light detection system in optical communication with said transducer; and
   wherein said transducer enters a higher energy state through the at least partial absorption of the excitation light and enters a lower energy state through radiation of emitted light in approximately 200 nanoseconds to produce spectral indicia that is indicative of the oxygen concentration in the fluid for processing by said light detection system.

2. The apparatus as recited in claim 1 wherein said excitation light source is selected from the group consisting of a light emitting diode, a laser diode, a non-diode laser, an incandescent device, and a fluorescent device.

3. The apparatus as recited in claim 1 wherein a fiber optic cable is disposed between said excitation light source and said transducer.

4. The apparatus as recited in claim 1 wherein said light detection system is selected from the group consisting of a spectrometer, photomultiplier tubes, diode detectors, charge coupled device (CCD) arrays, and diode arrays.

5. The apparatus as recited in claim 1 wherein a fiber optic cable is disposed between said transducer and said light detection system.

6. The apparatus as recited in claim 1 wherein said transducer is disposed at a terminus of a fiber optic cable.

7. The apparatus as recited in claim 1 wherein said transducer is made from a material that phosphoresces as it transitions between energy states.

8. The apparatus as recited in claim 7 wherein said transducer is made from a rare-earth metal doped phosphor material.

9. The apparatus as recited in claim 1 wherein said transducer is made from a material that fluoresces as it transitions between energy states.

10. The apparatus as recited in claim 9 wherein said transducer is made from an organometallic complex.

11. A method of rapidly measuring the oxygen concentration of a fluid with a sensing apparatus comprising the steps of:
   a. providing a transducer capable of photoluminescence and configured to be installed in an intake manifold of an internal combustion engine;
   b. energizing said transducer through the at least partial absorption of excitation light transmitted by an excitation light source that is in optical communication with said transducer;
   c. generating spectral indicia with said transducer as said transducer transitions to a higher energy state from a lower energy state through the at least partial absorption of the excitation light and as said transducer transitions to a lower energy state from the higher energy state through radiation of emitted light; and
   d. processing the spectral indicia with a light detection system that is in optical communication with said transducer to determine the oxygen concentration of the fluid; and
   wherein steps b, and c are performed in approximately 200 nanoseconds.

12. The method as recited in claim 11 wherein the optical communication of said energizing step is performed by a fiber optic cable.

13. The method as recited in claim 11 wherein the optical communication of said processing step is performed by a fiber optic cable.

14. The method as recited in claim 11 wherein the transducer of said providing step is comprised of a phosphorescent material.

15. The method as recited in claim 11 wherein the transducer of said providing step is comprised of a fluorescent material.

* * * * *